United States Patent
Wiener et al.

(10) Patent No.: US 6,662,127 B2
(45) Date of Patent: Dec. 9, 2003

(54) METHOD FOR DETECTING PRESENCE OF A BLADE IN AN ULTRASONIC SYSTEM

(75) Inventors: Eitan T. Wiener, Cincinnati, OH (US); Foster B. Stulen, Mason, OH (US); Allan L. Friedman, Cincinnati, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 156 days.

(21) Appl. No.: 09/866,911

(22) Filed: May 29, 2001

(65) Prior Publication Data

US 2002/0049552 A1 Apr. 25, 2002

Related U.S. Application Data

(60) Provisional application No. 60/242,169, filed on Oct. 20, 2000.

(51) Int. Cl.$^7$ .............................. G01R 9/00; A61B 17/32
(52) U.S. Cl. ............................. 702/75; 702/65; 702/106; 606/169
(58) Field of Search .............................. 702/33, 39, 56, 702/65, 72, 75, 106, 108, 113, 115, 116, 117, 119, 182, 183, 188, 189; 73/1.82, 606, 607, 618; 600/437–472, 441, 564, 568; 604/22; 606/128, 169, 49, 167, 168

(56) References Cited

U.S. PATENT DOCUMENTS

| | | | |
|---|---|---|---|
| 2,917,691 A | 12/1959 | DePrisco et al. | 318/118 |
| 4,965,532 A * | 10/1990 | Sakurai | 331/4 |
| 5,001,649 A | 3/1991 | Lo et al. | 364/484 |
| 5,026,387 A * | 6/1991 | Thomas | 606/169 |
| 5,042,460 A * | 8/1991 | Sakurai et al. | 606/128 |
| 5,112,300 A | 5/1992 | Ureche | 604/22 |
| 5,180,363 A | 1/1993 | Idemoto et al. | 202/32 |
| 5,387,190 A | 2/1995 | Gotanda et al. | 604/22 |
| 5,400,267 A | 3/1995 | Denen et al. | 364/552 |
| 5,406,503 A * | 4/1995 | Williams et al. | 702/106 |
| 5,425,704 A * | 6/1995 | Sakurai et al. | 604/22 |
| 5,431,664 A * | 7/1995 | Ureche et al. | 606/128 |
| 5,449,370 A | 9/1995 | Vaitekunas | 606/169 |
| 5,630,420 A | 5/1997 | Vaitekunas | 128/662.03 |
| 5,707,369 A | 1/1998 | Vaitekunas et al. | 606/31 |
| 5,879,364 A | 3/1999 | Bromfield et al. | 606/169 |
| 5,938,677 A * | 8/1999 | Boukhny et al. | 606/169 |
| 5,968,007 A | 10/1999 | Simon et al. | 604/22 |
| 6,017,354 A | 1/2000 | Culp et al. | 606/170 |
| 6,019,775 A * | 2/2000 | Sakurai | 606/169 |
| 6,027,515 A * | 2/2000 | Cimino | 606/169 |
| 6,066,135 A | 5/2000 | Honda | 606/39 |
| 6,090,123 A | 7/2000 | Culp et al. | 606/180 |
| 6,402,769 B1 * | 6/2002 | Boukhny | 606/169 |
| 2002/0002380 A1 * | 1/2002 | Bishop | 606/169 |

FOREIGN PATENT DOCUMENTS

| | | |
|---|---|---|
| JP | 2000-175926 | 6/2000 |
| WO | WO 95/09572 | 4/1995 |

OTHER PUBLICATIONS

European Search Report.

* cited by examiner

*Primary Examiner*—Marc S. Hoff
*Assistant Examiner*—Jeffrey R West
(74) *Attorney, Agent, or Firm*—Darby & Darby (57) ABSTRACT

The type of blade installed in a hand piece of an ultrasonic system is determined and the information used to adjust the fault detection threshold of the generator by using an impedance diagram to determine the type of blade which is connected to the hand piece. A check is performed to determine the magnitude of the blade impedance at resonance. If the hand piece is bare (i.e. no blade is attached), the magnitude of the impedance at resonance is typically less than 125 ohms. If on the other hand, a blade is connected, the impedance will be greater that 125 ohms. This value is used to indicated the presence or absence of a blade.

23 Claims, 6 Drawing Sheets

METHOD FOR DETECTING PRESENCE OF A BLADE IN AN ULTRASONIC SYSTEM

RELATED APPLICATIONS

The present invention relates to, and claims priority of, U.S. Provisional Patent Application Ser. No. 60/242,169 filed on Oct. 20, 2000, having the same title as the present invention, which is incorporated herein by reference.

BACKGROUND OF THE INVENTION

1. Field of the Invention

The present invention generally relates to ultrasonic surgical systems and, more particularly, to a method for using resonance characteristics to determine the presence and/or the type of blade in an ultrasonic system.

2. Description of the Related Art

It is known that electric scalpels and lasers can be used as a surgical instrument to perform the dual function of simultaneously effecting the incision and hemostatis of soft tissue by cauterizing tissues and blood vessels. However, such instruments employ very high temperatures to achieve coagulation, causing vaporization and fumes as well as splattering. Additionally, the use of such instruments often results in relatively wide zones of thermal tissue damage.

Cutting and cauterizing of tissue by means of surgical blades vibrated at high speeds by ultrasonic drive mechanisms is also well known. One of the problems associated with such ultrasonic cutting instruments is uncontrolled or undamped vibrations and the heat, as well as material fatigue resulting therefrom. In an operating room environment attempts have been made to control this heating problem by the inclusion of cooling systems with heat exchangers to cool the blade. In one known system, for example, the ultrasonic cutting and tissue fragmentation system requires a cooling system augmented with a water circulating jacket and means for irrigation and aspiration of the cutting site. Another known system requires the delivery of cryogenic fluids to the cutting blade.

It is known to limit the current delivered to the transducer as a means for limiting the heat generated therein. However, this could result in insufficient power to the blade at a time when it is needed for the most effective treatment of the patient. U.S. Pat. No. 5,026,387 to Thomas, which is assigned to the assignee of the present application and is incorporated herein by reference, discloses a system for controlling the heat in an ultrasonic surgical cutting and hemostasis system without the use of a coolant, by controlling the drive energy supplied to the blade. In the system according to this patent an ultrasonic generator is provided which produces an electrical signal of a particular voltage, current and frequency, e.g. 55,500 cycles per second. The generator is connected by a cable to a hand piece which contains piezoceramic elements forming an ultrasonic transducer. In response to a switch on the hand piece or a foot switch connected to the generator by another cable, the generator signal is applied to the transducer, which causes a longitudinal vibration of its elements. A structure connects the transducer to a surgical blade, which is thus vibrated at ultrasonic frequencies when the generator signal is applied to the transducer. The structure is designed to resonate at the selected frequency, thus amplifying the motion initiated by the transducer.

The signal provided to the transducer is controlled so as to provide power on demand to the transducer in response to the continuous or periodic sensing of the loading condition (tissue contact or withdrawal) of the blade. As a result, the device goes from a low power, idle state to a selectable high power, cutting state automatically depending on whether the scalpel is or is not in contact with tissue. A third, high power coagulation mode is manually selectable with automatic return to an idle power level when the blade is not in contact with tissue. Since the ultrasonic power is not continuously supplied to the blade, it generates less ambient heat, but imparts sufficient energy to the tissue for incisions and cauterization when necessary.

The control system in the Thomas patent is of the analog type. A phase lock loop (that includes a voltage controlled oscillator, a frequency divider, a power switch, a matching network and a phase detector), stabilizes the frequency applied to the hand piece. A microprocessor controls the amount of power by sampling the frequency, current and voltage applied to the hand piece, because these parameters change with load on the blade.

The power versus load curve in a generator in a typical ultrasonic surgical system, such as that described in the Thomas patent, has two segments. The first segment has a positive slope of increasing power as the load increases, which indicates constant current delivery. The second segment has a negative slope of decreasing power as the load increases, which indicates a constant or saturated output voltage. The regulated current for the first segment is fixed by the design of the electronic components and the second segment voltage is limited by the maximum output voltage of the design. This arrangement is inflexible since the power versus load characteristics of the output of such a system can not be optimized to various types of hand piece transducers and ultrasonic blades. The performance of traditional analog ultrasonic power systems for surgical instruments is affected by the component tolerances and their variability in the generator electronics due to changes in operating temperature. In particular, temperature changes can cause wide variations in key system parameters such as frequency lock range, drive signal level, and other system performance measures.

In order to operate an ultrasonic surgical system in an efficient manner, during startup the frequency of the signal supplied to the hand piece transducer is swept over a range to locate the resonance frequency. Once it is found, the generator phase lock loop locks on to the resonance frequency, continues to monitor the transducer current to voltage phase angle, and maintains the transducer resonating by driving it at the resonance frequency. A key function of such systems is to maintain the transducer resonating across load and temperature changes that vary the resonance frequency. However, these traditional ultrasonic drive systems have little to no flexibility with regards to adaptive frequency control. Such flexibility is key to the system's ability to discriminate undesired resonances. In particular, these systems can only search for resonance in one direction, i.e., with increasing or decreasing frequencies and their search pattern is fixed. The system cannot:

(i) hop over other resonance modes or make any heuristic decisions, such as what resonance to skip or lock onto, and
(ii) ensure delivery of power only when appropriate frequency lock is achieved.

The prior art ultrasonic generator systems also have little flexibility with regard to amplitude control, which would allow the system to employ adaptive control algorithms and decision making. For example, these fixed systems lack the ability to make heuristic decisions with regards to the output drive, e.g., current or frequency, based on the load on the blade and/or the current to voltage phase angle. It also limits the system's ability to set optimal transducer drive signal levels for consistent efficient performance, which would increase the useful life of the transducer and ensure safe operating conditions for the blade. Further, the lack of control over amplitude and frequency control reduces the system's ability to perform diagnostic tests on the transducer/blade system and to support troubleshooting in general.

Some limited diagnostic tests performed in the past involve sending a signal to the transducer to cause the blade to move and the system to be brought into resonance or some other vibration mode. The response of the blade is then determined by measuring the electrical signal supplied to the transducer when the system is in one of these modes. The ultrasonic system described in U.S. application Ser. No. 09/693,621, filed on Oct. 20, 2000, which is incorporated herein by reference, possesses the ability to sweep the output drive frequency, monitor the frequency response of the ultrasonic transducer and blade, extract parameters from this response, and use these parameters for system diagnostics. This frequency sweep and response measurement mode is achieved via a digital code such that the output drive frequency can be stepped with high resolution, accuracy, and repeatability not existent in prior art ultrasonic systems.

An increased level of information on the components of the ultrasonic generator, such as the hand piece and blade, permits the setting of higher fault tolerance levels. Without this ability to set "tight" tolerances (i.e., strict criteria), the impedance level at which a system is declared bad must be set at the highest possible impedance value associated with the hand piece/blade combination. In this case, the impedance value can be over 250 ohms, while a hand piece held in air connected to a test tip is known to possess a nominal impedance of approximately 25 ohms. Such a large difference in impedance values is problematic because any faults which occur must be catastrophic before they can be detected.

For best performance the generator, the hand piece and the blade, individually and together, must operate correctly. Otherwise the performance of the ultrasonic system will be degraded, and thus require troubleshooting to locate system faults. While continuing to operate with an inefficiency in the blade or the hand piece, discarding good blades and hand pieces can be time consuming and expensive. In order for a diagnostic system to be effective it must deal with an acceptable level of misses and false alarms. Prior art ultrasonic systems must have their fault tolerances set to take this criterion into consideration. The more restrictive the tolerance criteria, the more accurate the diagnostics become. As a result, less time will be spent in the operating room (OR) trouble shooting problems associated with the ultrasonic system. It is therefore important to keep the thresholds for fault detection relatively restricted, in comparison to the nominal operating range of the ultrasonic system.

SUMMARY OF THE INVENTION

The present invention is a method for determining whether a blade is connected to a hand piece which is connected to a generator in an ultrasonic surgical system. If so, the type of blade installed on the hand piece is determined and the information is used to adjust the fault detection threshold, to adjust test parameters and to adjust the overall operation of the generator. This is accomplished by using resonance characteristics to determine the type of blade which is connected to the hand piece. In the present invention, a hand piece is designed to resonate at a first frequency. A hand piece/blade combination is known to resonate at a second frequency. In accordance with the invention, to determine whether a hand piece is bare or whether a blade is attached, a check is performed to determine the resonance frequency. If the hand piece is bare (i.e. no blade is attached), the resonance frequency is within a first resonance range. In an embodiment of the invention, the blade type is determined by measuring the phase margin of the hand piece/blade. The difference in frequency between the anti-resonance (frequency with maximum impedance) and the resonance (frequency with minimum impedance) is the phase margin (PM) that is measured in hertz. The phase margin for a bare hand piece, a hand piece with a test tip or a hand piece with a blade is nominally 600 hertz, 200 hertz, and less than 180 hertz, respectively. In accordance with the invention, three thresholds are set for the phase margin to determine whether a blade that is operating under optimum conditions is attached to the hand piece.

BRIEF DESCRIPTION OF THE DRAWINGS

The foregoing and other advantages and features of the invention will become more apparent from the detailed description of the preferred embodiments of the invention given below with reference to the accompanying drawings in which.

DETAILED DESCRIPTION OF THE PREFERRED EMBODIMENTS

Figure 1:
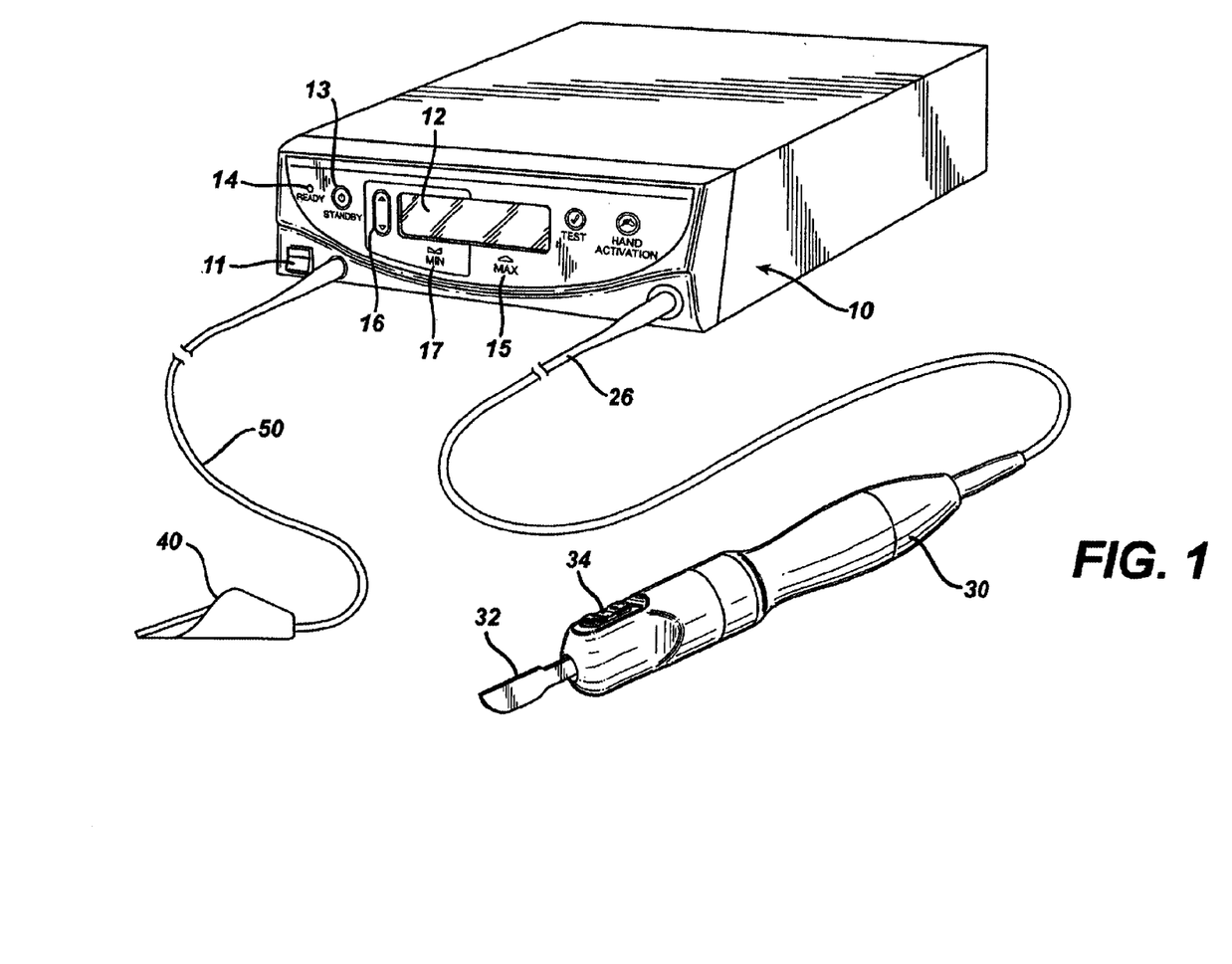
FIG. 1 is an illustration of a console for an ultrasonic surgical cutting and hemostasis system, as well as a hand piece and foot switch in which the method of the present invention is implemented.

FIG. 1 is an illustration of a system for implementing the method in according to the invention. By means of a first set of wires in cable 26, electrical energy, i.e., drive current, is sent from the console 10 to a hand piece 30 where it imparts ultrasonic longitudinal movement to a surgical device, such as a sharp scalpel blade 32. This blade can be used for simultaneous dissection and cauterization of tissue. The supply of ultrasonic current to the hand piece 30 may be under the control of a switch 34 located on the hand piece, which is connected to the generator in console 10 via wires in cable 26. The generator may also be controlled by a foot switch 40, which is connected to the console 10 by another cable 50. Thus, in use a surgeon may apply an ultrasonic electrical signal to the hand piece, causing the blade to vibrate longitudinally at an ultrasonic frequency, by operating the switch 34 on the hand piece with his finger, or by operating the foot switch 40 with his foot.

The generator console 10 includes a liquid crystal display device 12, which can be used for indicating the selected cutting power level in various means such, as percentage of maximum cutting power or numerical power levels associated with cutting power. The liquid crystal display device 12 can also be utilized to display other parameters of the system. Power switch 11 is used to turn on the unit. While it is warming up, the "standby" light 13 is illuminated. When it is ready for operation, the "ready" indicator 14 is illuminated and the standby light goes out. If the unit is to supply maximum power, the MAX button 15 is depressed. If a lesser power is desired, the MIN button 17 is activated. The level of power when MIN is active is set by button 16.

When power is applied to the ultrasonic hand piece by operation of either switch 34 or 40, the assembly will cause the surgical scalpel or blade to vibrate longitudinally at approximately 55.5 kHz, and the amount of longitudinal movement will vary proportionately with the amount of driving power (current) applied, as adjustably selected by the user. When relatively high cutting power is applied, the blade is designed to move longitudinally in the range of about 40 to 100 microns at the ultrasonic vibrational rate. Such ultrasonic vibration of the blade will generate heat as the blade contacts tissue, i.e., the acceleration of the blade through the tissue converts the mechanical energy of the moving blade to thermal energy in a very narrow and localized area. This localized heat creates a narrow zone of coagulation, which will reduce or eliminate bleeding in small vessels, such as those less than one millimeter in diameter. The cutting efficiency of the blade, as well as the degree of hemostasis, will vary with the level of driving power applied, the cutting rate of the surgeon, the nature of the tissue type and the vascularity of the tissue.

Figure 2:
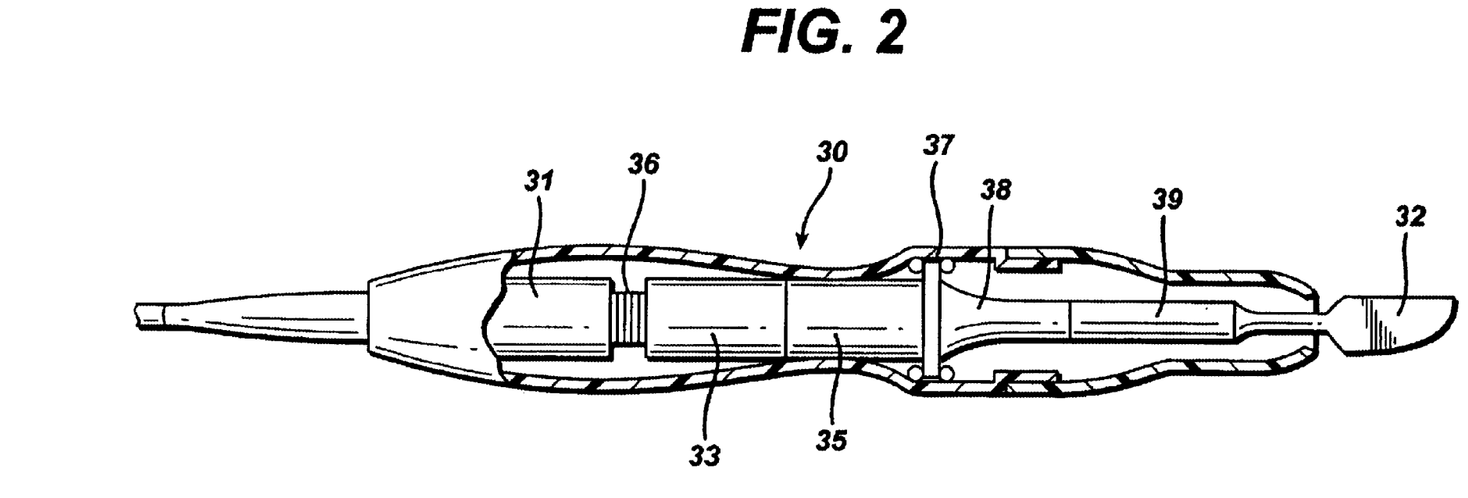
FIG. 2 is a schematic view of a cross section through the ultrasonic scalpel hand piece of the system of FIG. 1.

As illustrated in more detail in FIG. 2, the ultrasonic hand piece 30 houses a piezoelectric transducer 36 for converting electrical energy to mechanical energy that results in longitudinal vibrational motion of the ends of the transducer. The transducer 36 is in the form of a stack of ceramic piezoelectric elements with a motion null point located at some point along the stack. The transducer stack is mounted between two cylinders 31 and 33. In addition a cylinder 35 is attached to cylinder 33, which in turn is mounted to the housing at another motion null point 37.

A horn 38 is also attached to the null point on one side and to a coupler 39 on the other side. Blade 32 is fixed to the coupler 39. As a result, the blade 32 will vibrate in the longitudinal direction at an ultrasonic frequency rate with the transducer 36. The ends of the transducer achieve maximum motion with a portion of the stack constituting a motionless node, when the transducer is driven with a maximum current at the transducers' resonant frequency. However, the current providing the maximum motion will vary with each hand piece and is a valve stored in the non-volatile memory of the hand piece so the system can use it.

The parts of the hand piece are designed such that the combination will oscillate at the same resonant frequency. In particular, the elements are tuned such that the resulting length of each such element is one-half wavelength. Longitudinal back and forth motion is amplified as the diameter closer to the blade 32 of the acoustical mounting horn 38 decreases. Thus, the horn 38 as well as the blade/coupler are shaped and dimensioned so as to amplify blade motion and provide harmonic vibration in resonance with the rest of the acoustic system, which produces the maximum back and forth motion of the end of the acoustical mounting horn 38 close to the blade 32. A motion at the transducer stack is amplified by the horn 38 into a movement of about 20 to 25 microns. A motion at the coupler 39 is amplified by the blade 32 into a blade movement of about 40 to 100 microns.

Figure 3A:
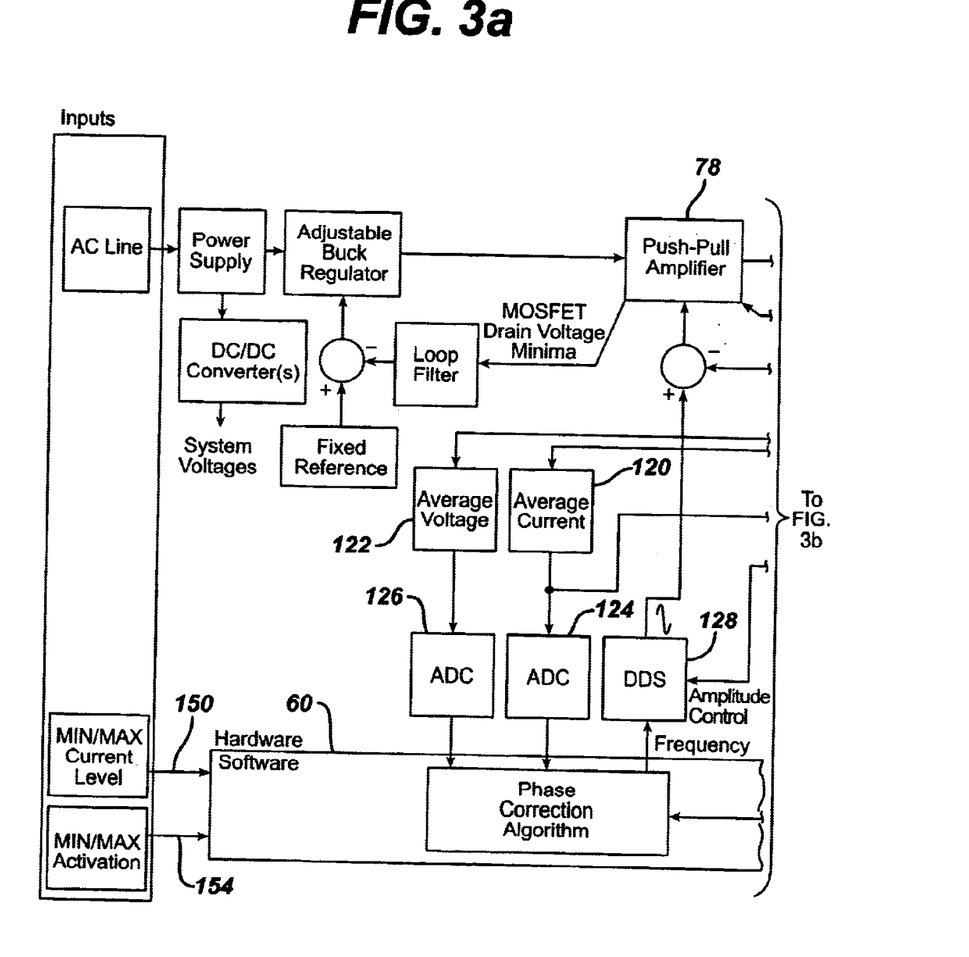
FIGS. 3(a) and 3(b) are block diagrams illustrating the ultrasonic generator in which a preferred embodiment of the invention is implemented.
Figure 3B:
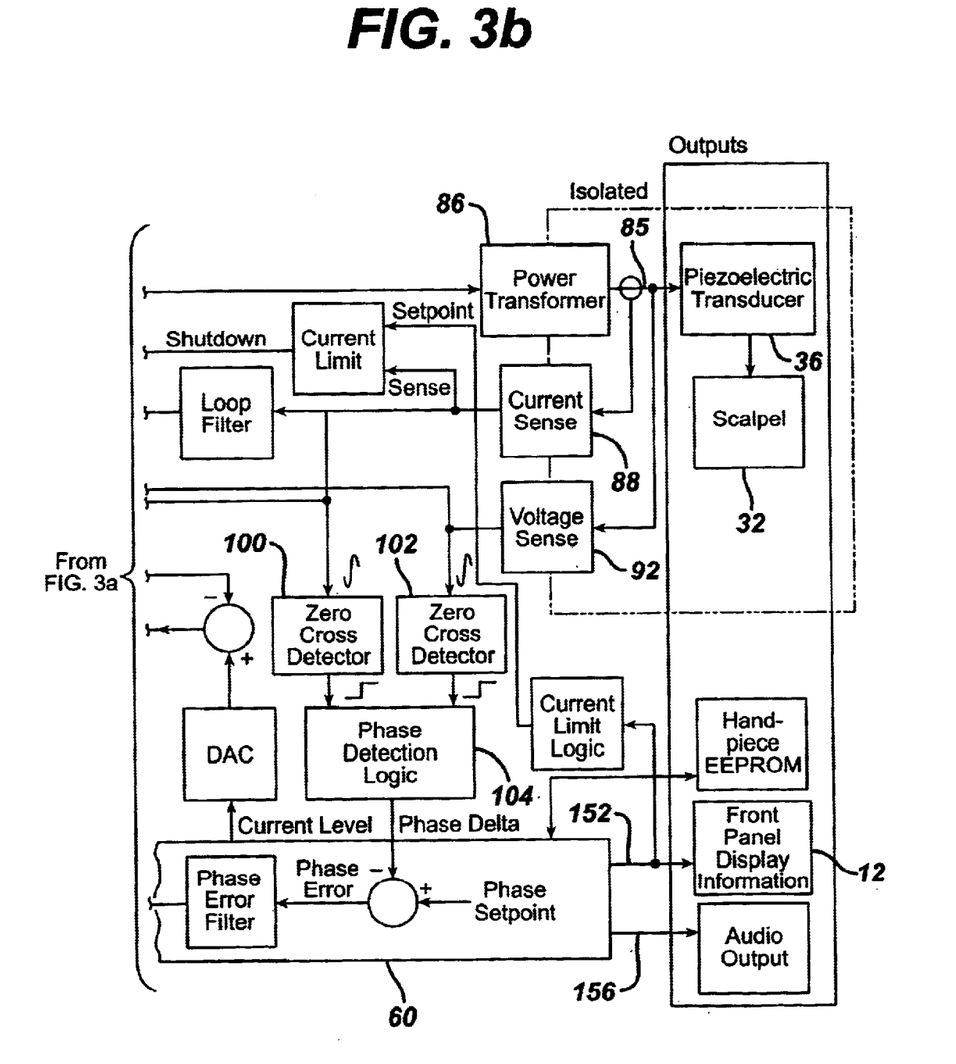

The system which creates the ultrasonic electrical signal for driving the transducer in the hand piece is illustrated in FIGS. 3(*a*) and 3(*b*). This drive system is flexible and can create a drive signal at a desired frequency and power level setting. A DSP 60 or microprocessor in the system is used for monitoring the appropriate power parameters and vibratory frequency as well as causing the appropriate power level to be provided in either the cutting or coagulation operating modes. The DSP 60 or microprocessor also stores computer programs which are used to perform diagnostic tests on components of the system, such as the transducer/blade.

For example, under the control of a program stored in the DSP or microprocessor 60, such as a phase correction algorithm, the frequency during startup can be set to a particular value, e.g., 50 kHz. It can than be caused to sweep up at a particular rate until a change in impedance, indicating the approach to resonance, is detected. Then the sweep rate can be reduced so that the system does not overshoot the resonance frequency, e.g., 55 kHz. The sweep rate can be achieved by having the frequency change in increments, e.g., 50 cycles. If a slower rate is desired, the program can decrease the increment, e.g., to 25 cycles which both can be based adaptively on the measured transducer impedance magnitude and phase. Of course, a faster rate can be achieved by increasing the size of the increment. Further, the rate of sweep can be changed by changing the rate at which the frequency increment is updated.

If it is known that there is a undesired resonant mode, e.g., at say 51 kHz, the program can cause the frequency to sweep down, e.g., from 60 kHz, to find resonance. Also, the system can sweep up from 50 kHz and hop over 51 kHz where the undesired resonance is located.

In any event, the system has a great degree of flexibility In operation, the user sets a particular power level to be used with the surgical instrument. This is done with power level selection switch 16 on the front panel of the console. The switch generates signals 150 that are applied to the DSP 60. The DSP 60 then displays the selected power level by sending a signal on line 152 (FIG. 3(*b*)) to the console front panel display 12.

To actually cause the surgical blade to vibrate, the user activates the foot switch 40 or the hand piece switch 34. This activation puts a signal on line 154 in FIG. 3(*a*). This signal is effective to cause power to be delivered from push-pull amplifier 78 to the transducer 36. When the DSP or microprocessor 60 has achieved lock on the hand piece transducer resonance frequency and power has been successfully applied to the hand piece transducer, an audio drive signal is put on line 156. This causes an audio indication in the system to sound, which communicates to the user that power is being delivered to the hand piece and that the scalpel is active and operational.

FIG. 4 is a parallel equivalent electrical circuit for mathematically modeling an ultrasonic transducer. The shunt capacitance C0 of the transducer is a parasitic circuit element and current flowing through it does not contribute to the motion of the blade. A parallel tuning inductor (Ls) is used in the ultrasonic generator to minimize the effects of C0. The capacitive reactance of C0 is canceled by the inductive reactance of the Ls. Currents which affect C0 and Ls result in a high impedance at the resonant frequency, and minimal losses due to the high Q of Ls. Variations in the resonant frequency, the values of C0 and the tuning inductor slightly de-tune the system. The equivalent load impedance of the tuned circuit is restricted to the motional components of the ultrasonic transducer. Voltage feedback capacitors (not shown), which reside at the amplifier output (not shown), are treated as part of C0 and are included in the calculation of the value of Ls.

Figure 4A:
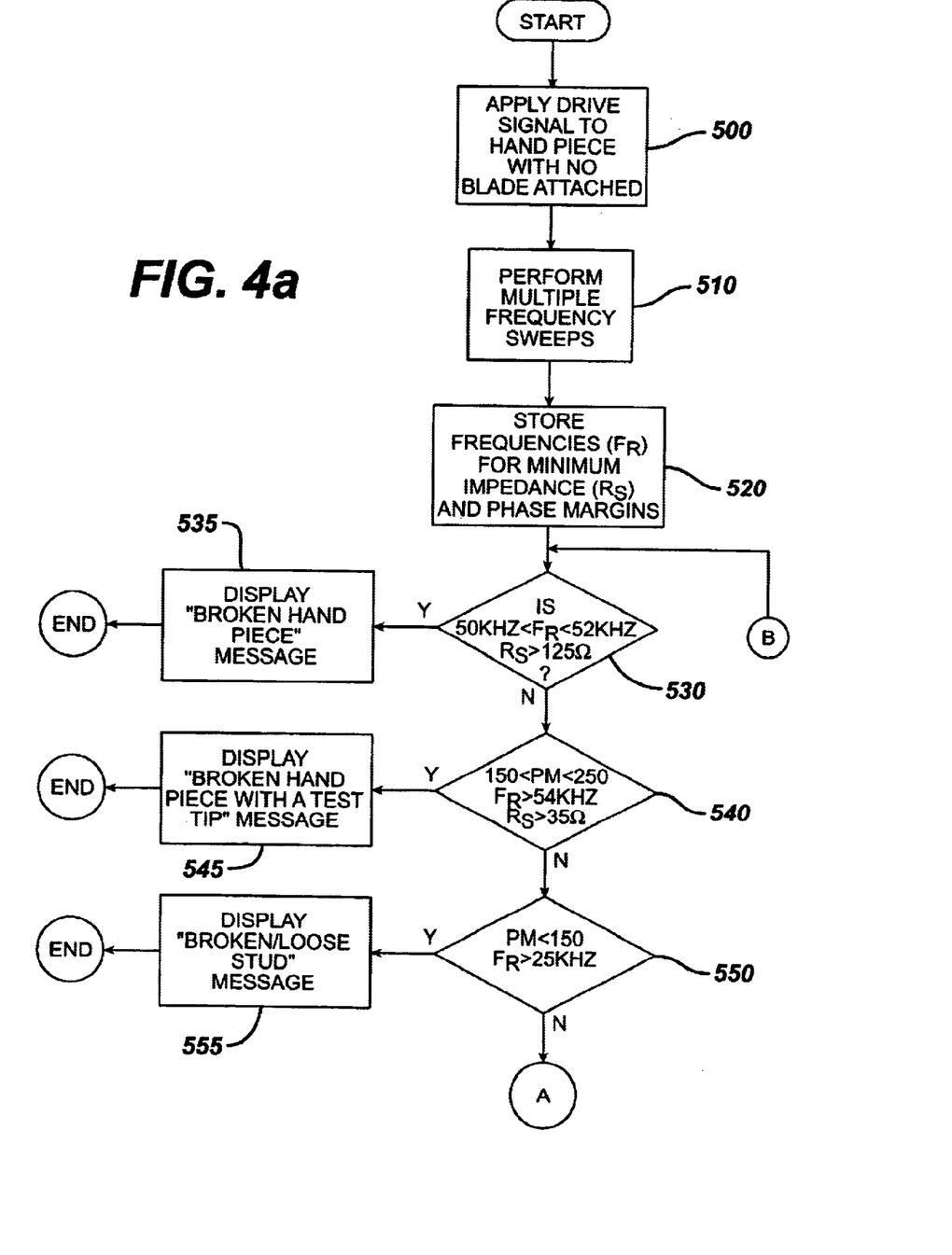
FIGS. 4(a) and 4(b) are flow charts illustrating the preferred embodiment of the method of the invention.
Figure 4B:
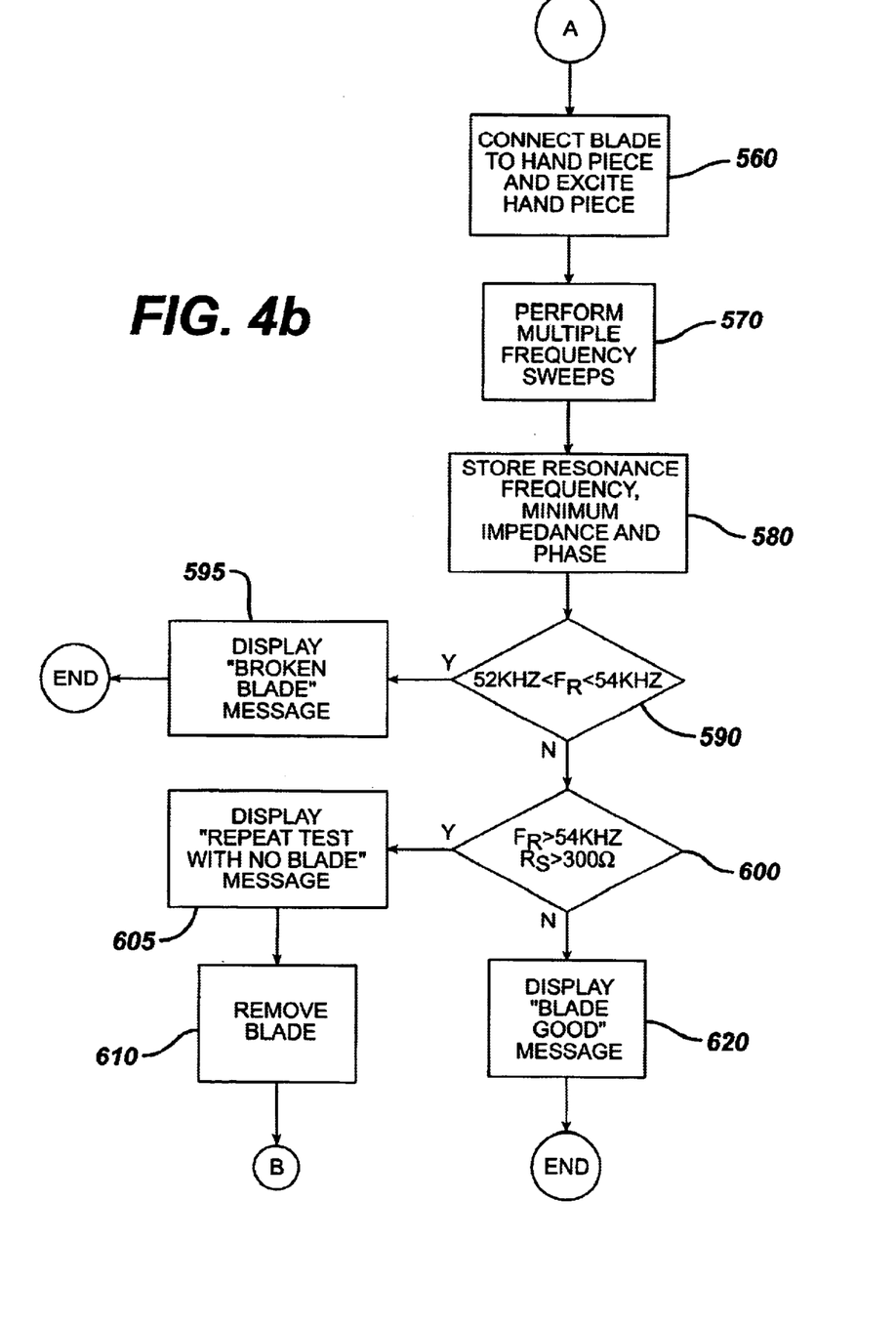

FIGS. 4(*a*) and 4(*b*) are flow charts illustrating a preferred embodiment of the method of the invention. Without a blade connected to the hand piece and under control of the program stored in the DSP or microprocessor 60 shown in FIGS. 3(*a*) and 3(*b*), the method of the invention is implemented by using the ultrasonic generator to excite the hand piece, as indicated in step 500. Frequency sweeps are performed in a target frequency range to determine the frequency at which minimum impedance occurs, as indicated in step 510. The resonance frequency (Fr) at which the minimum impedance occurs and the minimum impedance (Rs) for each of the sweeps is recorded and stored, as indicated in step 520. The phase margin (PM), which is the difference in frequency between the anti-resonance (frequency with maximum impedance) and the resonance (frequency with minimum impedance), for each sweep is also recorded. In the preferred embodiment, three sweeps and three resonance frequencies at which the minimum impedance occurs, the corresponding minimum impedance and phase margin values are recorded and stored (i.e., three minimum impedances and three minimum phases), and three corresponding phase margin values are used to determine true minimum impedance values). Here, the frequency sweeps are performed in the target range of 50 kHz to 56 kHz.

A check is performed to determine whether a resonance frequency (Fr) is between 50 kHz and 52 kHz, and whether Rs is greater than 125 ohms and whether the magnitude of the phase margin (PM) is greater than 250 Hz, as indicated in step 530. If this is the case, then a "Broken Hand Piece" message is displayed on the LCD 12, as indicated in step 535, and the test ends.

If the answer in step 530 is no, a test is performed to determine whether a test tip is connected to the system. In particular, the test (i) checks to see if the magnitude of the phase margin (PM) is between 150 and 250 Hertz, and (ii) whether Rs at the resonance frequency is greater than 35 ohms, as indicated in step 540. If this is the case, a "Broken Hand Piece with a Test Tip" message is displayed on the LCD 12, as indicated in step 545.

If the answer to step 540 is no, a test is performed to determine whether the magnitude of PM is less than 150 Hz, as indicated in step 550. If this is the case, a "Broken/Loose Stud" message is posted to the LCD 12, as indicated in step 555.

Next, if no error was displayed, a blade is connected to the hand piece, and the ultrasonic generator is used to excite the hand piece, as indicated in step 560. Three frequency sweeps are performed in the target range of 50 kHz to 56 kHz to determine the frequencies at which minimum impedance occurs, as indicated in step 570. The resonance frequency (Fr) at which minimum impedance occurs, the minimum impedance (Rs) and the phase margin (PM) are recorded and stored, as indicated in step 580.

A test is performed in step 590 to determine whether the resonance frequency (Fr) from any of the three steps is greater than 52 kHz, but less than 54 kHz. If this is the case, a "Broken Blade" message is displayed on the LCD 12, as indicated in step 595, and the test ends.

If the answer in step 590 is no, a further test is performed to determine whether the resonance frequency (Fr) is greater than 54 kHz and whether the corresponding minimum impedance (Rs) is greater than 300 ohms, as indicated in step 600. If this is the case, a "Repeat Test With No Blade" message is displayed on the LCD 12, as shown in step 605. Next, the blade is removed (step 610), and the test returns to step 530 where the hand piece is tested to determine if it is bad. If this is the case, a "Bad Hand Piece" message is displayed on the LCD 12, as indicated in step 535. If the answer in step 600 is no, i.e., fr is less than 54 kHz and Rs is less than 300 ohms, a "Good Blade" message is displayed on the LCD 12 in step 620 and the test is terminated.

During the test of the hand piece with a blade connected, the frequency of 54 kHz is used to ensure that the resonance frequency of the hand piece and blade does not fall below this value, which would indicate unsafe temperatures. Note, the 300 ohm impedance value is used to distinguish from blades which typically have impedances lower than 300 ohms. In addition, the value of phase margin (PM) is measured and stored, and it is known to be less than 150 Hz (as determined by step 540).

In addition, a dirty hand piece/blade attachment can lead to higher than expected impedances. Therefore, in the case of a test tip, a user is instructed to first clean the attachment and then remount the test tip prior to re-running the diagnostic procedures. This is performed in conjunction with the start of the test or during step 610.

In order to obtain the impedance measurements and impedance phase measurements (i.e., the frequency difference between resonance (e.g. minimum impedance) and anti-resonance (e.g. maximum impedance)), the DSP 60 and the other circuit elements of FIG. 4 are used. In particular, push-pull amplifier 78 delivers the ultrasonic signal to a power transformer 86, which in turn delivers the signal over a line 85 in cable 26 to the piezoelectric transducers 36 in the hand piece. The current in line 85 and the voltage on that line are detected by current sense circuit 88 and voltage sense circuit 92. The current and voltage sense signals are sent to average voltage circuit 122 and average current circuit 120, respectively, which take the average values of these signals. The average voltage is converted by analog-to-digital converter (ADC) 126 into a digital code that is input to DSP 60. Likewise, the current average signal is converted by analog-to-digital converter (ADC) 124 into a digital code that is input to DSP 60. In the DSP the ratio of voltage to current is calculated on an ongoing basis to give the present impedance values as the frequency is changed. A significant change in impedance occurs as resonance is approached.

The signals from current sense 88 and voltage sense 92 are also applied to respective zero crossing detectors 100, 102. These produce a pulse whenever the respective signals cross zero. The pulse from detector 100 is applied to phase detection logic 104, which can include a counter that is started by that signal. The pulse from detector 102 is likewise applied to logic circuit 104 and can be used to stop the counter. As a result, the count which is reached by the counter is a digital code on line 140, which represents the difference in phase between the current and voltage. The size of this phase difference is also an indication of resonance. These signals can be used as part of a phase lock loop that cause the generator frequency to lock onto resonance, e.g., by comparing the phase delta to a phase set point in the DSP in order to generate a frequency signal to a direct digital synthesis (DDS) circuit 128 that drives the push-pull amplifier 78.

Further, the impedance and phase values can be used as indicated above in a diagnosis phase of operation to detect if the blade is loose. In such a case the DSP does not seek to establish phase lock at resonance, but rather drives the hand piece at particular frequencies and measures the impedance and phase to determine if the blade is tight.

Using the method of the invention, the speed at which faults associated with the blade are diagnosed is increased. This reduces the time surgeons spend in the operating room trouble shooting problems associated with the ultrasonic system.

Although the invention has been described and illustrated in detail, it is to be clearly understood that the same is by way of illustration and example, and is not to be taken by way of limitation. The spirit and scope of the present invention are to be limited only by the terms of the appended claims.

What is claimed is:

1. A method for detecting presence of a blade in an ultrasonic surgical system, comprising the steps of:
    applying a drive signal to a hand piece without the blade attached using an ultrasonic generator;
    performing multiple frequency sweeps across a predetermined frequency range; storing a resonance frequency value, a minimum impedance value, and a phase margin value of the hand piece across the predetermined frequency range at the minimum impedance value of the hand piece;
    determining whether the resonance frequency value, the phase margin value and the minimum impedance value of the hand piece are within acceptable limits;
    if the resonance frequency value, the phase margin value and the minimum impedance value of the hand piece are within acceptable limits, connecting the blade to the hand piece and re-exciting the hand piece/blade with the drive signal across the predetermined frequency range;
    storing the resonance frequency value and the phase margin value of the hand piece/blade across the predetermined frequency range at the minimum impedance value of the hand piece/blade; and
    if the resonance frequency value and the minimum impedance value of the hand piece/blade are within acceptable limits, displaying a message on a liquid crystal display of the generator.

2. The method of claim 1, wherein the step of applying the drive signal comprises exciting the hand piece with an ultrasonic signal across a predetermined target frequency range without a blade attached to the hand piece.

3. The method of claim 2, wherein the predetermined target frequency range is from 50 kHz to 56 kHz.

4. The method of claim 1, wherein the multiple frequency sweeps across the predetermined frequency range are performed in a range from 50 kHz to 56 kHz.

5. The method of claim 4, wherein three frequency sweeps are performed.

6. The method of claim 1, wherein said determining step comprises: determining whether the resonance frequency is greater than 50 kHz and less than 52 kHz, the phase margin is greater than 250 Hz, and the minimum impedance value is greater than 350 ohms.

7. The method of claim 6, further comprising the step of:
    displaying the message on the liquid crystal display of the generator, if at least one of the resonance frequency, the phase margin and the minimum impedance of the hand piece is within the acceptable limits.

8. The method of claim 7, wherein the step of displaying the message comprises displaying a "Bad Hand Piece" message on the liquid crystal display.

9. The method of claim 6, further comprising the step of: determining whether a test tip is connected to the hand piece.

10. The method of claim 9, wherein the step of determining whether a test tip is connected to the hand piece comprises:
    determining whether the resonance frequency is greater than 54 KHz, the phase margin is greater than 150 Hz and less than 250 Hz, and the minimum impedance is greater than 35 Ohms.

11. The method of claim 10, further comprising the step of:
    displaying the message on the liquid crystal display of the generator, if the resonance frequency and minimum impedance and the phase margin of the hand piece are within the acceptable limits.

12. The method of claim 11, wherein the step of displaying the message comprises displaying a "Broken Hand Piece with a Test Tip" message on the liquid crystal display.

13. The method of claim 10, further comprising the step of:
    determining whether the phase margin is less than 150 Hz and the resonance frequency is greater than 25 KHz.

14. The method of claim 10, further comprising the step of:
    displaying the message on the liquid crystal display of the generator, if the phase margin is less than 150 Hz and the resonance frequency is greater than 25 KHz.

15. The method of claim 14, wherein the step of displaying the message comprises displaying a "Broken/Loose Stud" message on the liquid crystal display.

16. The method of claim 1, further comprising the steps of:
    determining whether the resonance frequency is greater than 52 kHz and less than 54 kHz.

17. The method of claim 16, further comprising the step of:
    displaying the message on the liquid crystal display of the generator, if the resonance frequency of the hand piece/blade is within the acceptable limits.

18. The method of claim 17, wherein the step of displaying the message comprises displaying a "Broken Blade" message on the liquid crystal display.

19. The method of claim 10, further comprising the steps of:
    determining whether
    the resonance frequency is greater than 54 kHz; and
    the minimum impedance is less than 300 ohms.

20. The method of claim 19, further comprising the step of:
    displaying the message on the liquid crystal display of the generator, if the hand piece/blade resonance frequency and the minimum impedance are greater than 54 kHz and less than 300 ohms, respectively.

21. The method of claim 20, wherein the step of displaying the message comprises displaying a "Good Blade" message on the liquid crystal display.

22. The method of claim 19, further comprising the step of:
    displaying the message on the liquid crystal display of the generator, if the hand piece/blade resonance frequency and the minimum impedance is less than 54 kHz and less than 300 ohms, respectively;
    removing the blade; and
    returning to the step of determining whether the test tip is connected to the hand piece.

23. The method of claim 22, wherein the step of displaying the message comprises displaying a "Repeat Test With No Blade" message on the liquid crystal display.

* * * * *